United States Patent [19]
Duvert et al.

[11] Patent Number: 5,977,156
[45] Date of Patent: *Nov. 2, 1999

[54] FUNGICIDAL PYRAZOLES

[75] Inventors: Patrice Duvert, Lyons, France; Dang Long Nguyen, Hochiminville, Viet Nam

[73] Assignee: Rhone-Poulenc Agrochimie, Lyon, France

[*] Notice: This patent issued on a continued prosecution application filed under 37 CFR 1.53(d), and is subject to the twenty year patent term provisions of 35 U.S.C. 154(a)(2).

[21] Appl. No.: 08/805,914

[22] Filed: Mar. 4, 1997

[30] Foreign Application Priority Data

Mar. 4, 1996 [FR] France ................................. 9602985
Jun. 19, 1996 [FR] France ................................. 9607831

[51] Int. Cl.⁶ .................... A01N 43/40; A01N 43/56; A61K 31/54; A61K 31/535
[52] U.S. Cl. ............... 514/404; 514/222.5; 514/223.8; 514/226.8; 514/227.5; 514/229.2; 514/236.5; 514/407; 514/340
[58] Field of Search .................. 514/404, 407, 514/340, 222.5, 223.8, 226.8, 227.5, 229.2, 236.5

[56] References Cited

U.S. PATENT DOCUMENTS

| | | | |
|---|---|---|---|
| 4,772,608 | 9/1988 | Sasse et al. | 514/275 |
| 4,804,675 | 2/1989 | Jensen-Korte et al. | 514/407 |
| 4,806,540 | 2/1989 | Sasse et al. | 514/236.5 |
| 4,820,725 | 4/1989 | Jensen-Korte et al. | 514/407 |
| 4,945,165 | 7/1990 | Jensen-Korte et al. | 548/362 |
| 5,175,176 | 12/1992 | Sasse et al. | 514/341 |
| 5,232,940 | 8/1993 | Hatton et al. | 514/407 |
| 5,292,744 | 3/1994 | Sasse et al. | 514/275 |
| 5,306,694 | 4/1994 | Phillips et al. | 504/253 |
| 5,547,974 | 8/1996 | Hatton et al. | 514/406 |

FOREIGN PATENT DOCUMENTS

| | | |
|---|---|---|
| 18075/95 | 9/1995 | Australia . |
| 1188856 | 6/1985 | Canada . |
| 0047850 | 3/1982 | European Pat. Off. . |
| 0201852 | 11/1986 | European Pat. Off. . |
| 0212281 | 3/1987 | European Pat. Off. . |
| 0216102 | 4/1987 | European Pat. Off. . |
| 0295117 | 12/1988 | European Pat. Off. . |
| 0469357 | 2/1992 | European Pat. Off. . |
| 0500209 | 8/1992 | European Pat. Off. . |
| 0627423 | 12/1994 | European Pat. Off. . |
| 4405207 | 8/1995 | Germany . |
| 87/03781 | 7/1987 | WIPO . |
| 93/06089 | 4/1993 | WIPO . |
| 94/21606 | 9/1994 | WIPO . |

OTHER PUBLICATIONS

Giori et al, *Il Farmaco—Ed. Sc.*—vol. 38, No. 4, pp. 274–282 (Apr. 1983).
Database Cropu, abstract No. 96–87998 (1995) and Yanni et al, *Eur. J. Plant Pathol.*, 101, Suppl. 1404 (1995).

*Primary Examiner*—Allen J. Robinson
*Attorney, Agent, or Firm*—Burns, Doane, Swecker & Mathis, L.L.P.

[57] ABSTRACT

Method for protecting plants against fungal or bacterial attack, which comprises applying a 1-phenyl-pyrazole or 1-(2-pyridyl)pyrazole.

39 Claims, No Drawings

FUNGICIDAL PYRAZOLES

BACKGROUND OF THE INVENTION

1. Field of the Invention

The present invention relates to a method for treating plants or wood against fungal or bacterial attack.

2. Description of the Related Art

Various 1-phenylpyrazoles and 1-(2-pyridyl)-pyrazoles are known as insecticides. For example, International Patent Publication No. WO 87/03781 and European Patent Publication No. 0295117 describe insecticidal 1-(substituted phenyl)pyrazoles. Also, International Patent Publications No. WO 93/06089 and WO 94/21606 describe insecticidal 1-(4-SF$_5$ substituted phenyl)-heterocycles which may be pyrroles or imidazoles or pyrazoles.

OBJECTS AND SUMMARY OF THE INVENTION

A first object of the invention is to control fungal or bacterial disease curatively or preventatively.

Another object of the present invention is to protect plants or wood against fungal or bacterial attack or disease.

Another object of the present invention is to protect rice, maize, cereal and cotton crops against fungal or bacterial attack or disease.

Another object of the present invention is to protect plants or wood against attack by fungi, said attack possibly being in conjunction with attack by insects.

Another object of the present invention is to protect plants or wood, by a treatment using a single product, against both attack by fungi and attack by insects or arthropods.

In other words again, another object of the present invention is to protect plants or wood, by a single treatment, using a single product effective both against attack by fungi and attack by insects or arthropods.

A particular object of the invention is to protect plants against fungal or bacterial attack or disease selected from the group consisting of those which appear in the following table:

| No. | English term | Latin term |
|---|---|---|
| 1 | Sheath blight | *Rhizoctonia solani*, also called *Pellicularia sasakii* |
| 2 | Brown spot | *Helminthosporium oryzae*, also called *Cochliobolus miyabeanus* |
| 3 | Leaf blast | *Pyricularia oryzae*, also called *Magnaporthe grisae* |
| 4 | Neck blast | *Pyricularia oryzae* |
| 5 | Leaf scald = leaf tip blight | *Rhynchosporium oryzae*, also called *Monographella albescens*, also called *Gerlachia oryzae* |
| 6 | Sheath rot | *Acrocylindrium oryzae* (also called *Sarocladium oryzae*) and/or *Gaeumannomyces graminis* (also called *Ophiobolus oryzinus*) and/or *Helminthosporium oryzae* |
| 7 | Grain discoloration | Bacteria: *Pseudomonas avenae*, *Pseudomonas syringae*, *Pseudomonas glumae*, *Pseudomonas fuscovaginae*, and/or *Erwinia herbicola*; and/or Fungi: *Helminthosporium oryzae* and/or *Alternaria spp.* |

Sheath rot corresponds to the harmful effect due to one or other or more than one of the various fungi mentioned in the above table.

Grain discoloration corresponds to the result of the destructive effect of a complex array of fungi and pathogenic bacteria, it being possible for the harmful result to be due to one or other or more than one of the various fungi or bacteria mentioned in the above table.

Yet another particular object of the invention is to protect plants against fungal or bacterial attack or disease selected from the group consisting of those which appear in the following table:

| No. | English term | Latin term |
|---|---|---|
| 8 | head smut | *Sphacelotheca reiliana* |
| 9 | root rot | *Fusarium moniliforme* |
| 10 | snow mould | *Microdochium nivale* |
| 11 | brown rust | *Puccinia recondita* |
| 12 | leaf stripe | *Pyrenophora graminea* |
| 13 | damping off | *Rhizoctonia solani* |
| 14 | dry and wet rots | *Serpula lacrymans* and *Coniophora puteana* |
| 15 | timber gill polypore | *Gloeophyllum trabeum* |

It has now been found that these aims may be achieved in whole or in part by means of the method according to the invention.

The present invention thus provides a method for protecting plants, e.g. crop plants, or wood against fungal or bacterial attack, which comprises applying to said plants, to the locus in which they grow or to said wood, a 1-phenylpyrazole or 1-(2-pyridyl)pyrazole in a fungicidally or bactericidally effective amount.

The 1-phenylpyrazoles and 1-(2-pyridyl)pyrazoles capable of being used in the invention are advantageously compounds of formula (I):

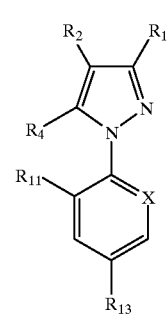

(I)

in which:

R$_1$ is CN or methyl;

$R_2$ is $S(O)_nR_3$;

$R_3$ is alkyl or haloalkyl;

$R_4$ represents a hydrogen or halogen atom or an $NR_5R_6$, $S(O)_mR_7$, $C(O)R_7$, $C(O)O-R_7$, alkyl, haloalkyl, $OR_8$ or $-N=C(R_9)(R_{10})$ radical;

$R_5$ and $R_6$ each independently represent a hydrogen atom or an alkyl, haloalkyl, $C(O)$alkyl or $S(O)_rCF_3$ radical, or $R_5$ and $R_6$ together form a divalent alkylene radical which is optionally interrupted by one or two divalent heteroatoms, such as oxygen or sulfur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl radical optionally having one or more substituents selected from the group consisting of halogen, OH, —O-alkyl, —S-alkyl, cyano and alkyl;

X represents a trivalent nitrogen atom or a C—$R_{12}$ radical, the three other valencies of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group; and m, n, q and r each represent, independently of one another, an integer equal to 0, 1 or 2;

with the proviso that, when $R_1$ is methyl, then $R_3$ is haloalkyl, $R_4$ is $NH_2$, $R_{11}$ is Cl, $R_{13}$ is $CF_3$ and X is N.

DETAILED DESCRIPTION OF THE INVENTION AND PREFERRED EMBODIMENTS

The crops to which the method according to the invention relates are, in particular, rice, maize, cereals, such as wheat and barley, and cotton.

Rice is a preferred crop for the implementation of the method according to the invention.

The protection conferred on wood is advantageous whether it concerns furniture wood or structural timber, on the one hand, or wood exposed to bad weather, such as fencing wood, vine stakes or railway sleepers, on the other hand.

More precisely, the invention further relates to a method for protecting crops and wood against fungal or bacterial attack and attack by arthropods or insects, these two kinds of attack being simultaneous or it being possible for these two kinds of attack to be simultaneous or these two kinds of attack being expected to be able to take place in the same time period.

The invention further relates to a method for protecting:

rice crops against fungal or bacterial attack, such as sheath blight, brown spot, neck blast, leaf blast and leaf scald;

maize crops, in particular against head smut and root rot;

wheat crops, in particular against root rot and rust;

barley crops, in particular against leaf stripe;

cotton crops, in particular against damping off.

The invention also relates to a method for protecting wood against fungi which degrade it and in particular against *Serpula lacrymans* and *Conicophora puteana*, and *Gloeophyllum trabeum*.

In practice, the protection imparted to crops or wood by 1-phenylpyrazoles or 1-(2-pyridyl)pyrazoles is generally better with respect to insects or arthropods. With respect to fungal or bacterial attack, the protection imparted by the products according to the invention may not be perfect but it is in general satisfactory and, in any case, it constitutes a very valuable complement to the insecticidal or arthropodicidal activity in giving the greatest possible protection to crops and wood against the most varied external attacks. Thus, a single treatment step, that is, applying a compound of formula (I) to plants, to the locus in which they grow or to wood, in an amount which is effective both as an arthropodicide (especially, as an insecticide), and as a fungicide or bactericide, can achieve protection not only against arthropods such as insects but can surprisingly also afford valuable protection against fungi and bacteria.

The alkyl radicals in the definition of formula (I) generally contain from 1 to 6 carbon atoms.

When $R_5$ and $R_6$ together with the nitrogen atom to which they are attached form a ring, the ring is generally 5- or 6-membered.

A preferred class of compounds of formula (I) is composed of the compounds such that $R_1$ is CN and/or $R_3$ is haloalkyl and/or $R_4$ is $NH_2$ and/or $R_{11}$ is a halogen atom and/or $R_{12}$ is a halogen atom and/or $R_{13}$ is haloalkyl.

When $R_{10}$ is a heteroaryl radical, it has 5 or 6 ring atoms, 1 to 3 of which are heteroatoms selected from the group consisting of O, S and N. Illustrative heteroaryl radicals are pyridyl, thienyl, furanyl and pyrrolyl.

A compound of formula (I) which is very particularly preferred in the invention is 1-[2,6-$Cl_2$-4-$CF_3$phenyl]-3-CN-4-[SO-$CF_3$]-5-$NH_2$pyrazole, i.e. 5-amino-3-cyano-1-(2,6-dichloro-4-trifluoromethyl)phenyl-4-trifluoromethylsulfinylpyrazole, hereinafter known as Compound A.

Compounds of formula (I) can be prepared according to one or other of the processes described in International Patent Publications No. WO 87/03781, 93/06089 or 94/21606 or European Patent Publication No. 0295117 or any other process coming within the competence of the person skilled in the art of chemical synthesis.

Formulations which can be used in the invention are described in particular in International Patent Publications No. WO 87/03781, 93/06089 and 94/21606 and in European Patent Publication No. 0295117. The formulations described in the prior art can be adapted to specific usage herein depending on local conditions, in particular by additions of appropriate adjuvants.

The 1-arylpyrazoles used in the present invention, i.e., 1-phenylpyrazoles and 1-(2-pyridyl)pyrazoles of formula (I), can advantageously be formulated as fluid or liquid compositions, wettable powders or microemulsions. Such formulations generally comprise one or more solid or liquid, inert vehicles or diluents which are agronomically acceptable in the case of application to cultivated areas.

The formulations which are suitable for the implementation of the method according to the invention generally comprise from about 0.0001 to about 95% by weight of active material of formula (I). As regards concentrated formulations for commercial use (for storage, sale or transportation), they advantageously comprise from about 0.1 to about 15% by weight of active material. The compositions as used by the applicator are generally much more dilute compositions. In addition to this active material, the compositions according to the invention may contain various vehicles, which may be solid or liquid, surfactants and other adjuvants of the most varied natures but which are agronomically acceptable.

Wettable powder or concentrated granule formulations can be prepared by milling a 1-arylpyrazole of formula (I)

with approximately 1% to approximately 20% by weight of solid anionic surfactant. A suitable anionic surfactant is the dioctyl ester of the sodium salt of sulfosuccinic acid. Approximately 85% to approximately 95% by weight of inert diluent, such as montmorillonite, attapulgite, chalk, talc, kaolin, diatomaceous earth, pumice, silicates or other similar products, can be included in such formulations, as well as the other adjuvants indicated above.

In addition to the granules and wettable powders described above, use may be made of fluid formulations, and in particular of formulations which are easily dispersible in water, in order to facilitate dispersion over the application site, in particular in agriculture.

The pyrazoles used in the present invention have a low solubility but can be used at low doses. They can therefore be used in solutions or emulsions or, preferably, in the form of aqueous or non-aqueous suspensions comprising appropriate adjuvants and/or cosolvents. Acetone and methyl ethyl ketone can be used as cosolvents. Any liquid medium can be used, provided that it is neither toxic to plants nor to the environment. When the active material has little solubility, cosolvents and/or wetting or dispersing agents can be used. Other additives can also be used, such as talc. The active materials of formula (I) can be absorbed on vehicles, for example vermiculite, clay, talc, kaolin or others, in particular in order to form granules.

The 1-arylpyrazoles of the invention can be used, in the case of plants, in leaf treatment or in soil treatment or, preferably, in seed treatment. The exact amount of arylpyrazole used can be determined by a small number of experiments. The amount must not be phytotoxic.

The 1-arylpyrazoles of the invention can be used, in the case of wood, by injection, impregnation or spraying according to processes known per se. The dose of 1-arylpyrazole applied is then from about 10 to about 800 g/m$^3$ of wood, preferably from about 50 to about 500 g/m$^3$.

In practice, the doses applied to the plants, either directly via the foliage or via the soil or by means of treated seeds, are generally of from about 5 to about 500 g/ha, preferably from about 10 to about 200 g/ha, and more preferentially still from about 20 to about 80 g/ha. The dose applied to the seed depends on the amount of seed sown. Once the seed has been sown, the dose contributed to the soil by means of the treated grains corresponds to that which has just been shown. In the case of rice, the amounts of seeds sown are of the order of from about 0.5 to about 3 quintals per ha.

The seeds can be treated by coating, covering, impregnation or steeping in liquid or pasty formulations. Such formulations are known per se. In general, a subsequent drying is carried out.

Treated seeds most often comprise from about 1 to about 1000 g of 1-arylpyrazole per 100 kg of seeds, preferably from about 2 to about 800 g/100 kg and more preferentially still from about 5 to about 500 g/100 kg.

When, according to a preferred alternative form of the invention, the treated seed is a rice seed, said seed advantageously comprises from about 2 to about 200 g of 1-arylpyrazole per 100 kg of seeds, preferably from about 5 to about 80 g/100 kg.

In the case of cereals, the treated seeds most often comprise from about 5 to about 250 g of 1-arylpyrazole per 100 kg of seeds, preferably from about 10 to about 100 g/100 kg.

In the case of maize, the treated seeds most often comprise from about 50 to about 1000 g of 1-arylpyrazole per 100 kg of seeds, preferably from about 100 to about 500 g/100 kg.

In the case of cotton, the treated seeds most often comprise from about 50 to about 500 g of 1-arylpyrazole per 100 kg of seeds, preferably from about 100 to about 250 g/100 kg.

The following examples, given without implied limitation, illustrate the invention and show how it can be implemented. In these examples, the active material used is Compound A.

EXAMPLE 1

Rice seeds were treated in the proportion of 40 g of active material per 100 kg. The seeds were sown in the proportion of 150 kg/ha on dry ground and the seeds were covered with a fine layer of earth.

These sown grains were left to germinate. After a few weeks, where the temperature was between 25° C. and 35° C., the soil was covered with water as a result of rain and the results were observed after 2 months. The trials were repeated on 20 plots, each of 10 m$^2$ (harvest after approximately 105 days).

The results shown in Table 1 (expressed as a percentage) were obtained, these results being measured by visual appraisal with respect to the control consisting of similar plots of cultivated ground treated using customary insecticides (in practice carbofuran or the pyrethroids) at the normally active doses.

EXAMPLE 2

Example 1 is repeated but sowing the seeds in the proportion of 200 kg/ha.

The results shown in Table 1 were obtained.

EXAMPLE 3

Example 1 is repeated but carrying out a pregermination of the rice seed.

The results shown in Table 1 were obtained.

EXAMPLE 4

Example 2 is repeated but carrying out a pre-germination of the rice seed.

The results shown in Table 1 were obtained.

TABLE 1

| Attack of type No. | Property observed in order to determine the result | Result observed, expressed as percentage | | | |
|---|---|---|---|---|---|
| | | Ex. 1 | Ex. 2 | Ex. 3 | Ex. 4 |
| 1 | number of sheaths attacked | 55 | 60 | 55 | 60 |
| 2 | area of leaves attacked | 79 | 87 | 79 | 87 |
| 3 | number of sheaths attacked | 82 | 90 | 82 | 90 |
| 4 | number of plants attacked just below the ear | 35 | 39 | 35 | 39 |
| 5 | number of leaves having a withered part | 57 | 63 | 57 | 63 |
| 6 | number of sheaths attacked | 80 | 88 | 80 | 88 |

TABLE 1-continued

| Attack of type No. | Property observed in order to determine the result | Result observed, expressed as percentage | | | |
|---|---|---|---|---|---|
| | | Ex. 1 | Ex. 2 | Ex. 3 | Ex. 4 |
| 7 | number of grains in which the normal yellow color is replaced by brown blemishes | 63 | 70 | 63 | 70 |

EXAMPLE 5

This example illustrates application against head smut (*Sphacelotheca reiliana*).

Maize seeds (variety Adonis) were treated in the proportion of 250 g of active material per 100 kg of seeds.

These seeds are sown in 9×9 cm pots filled with a mixture of compost and coarse sand which has been pre-infected by incorporation of *Sphacelotheca reiliana* spores according to 2 infectious doses: 0.125 and 0.25 of spores per kg of substrate. Each pot contains 5 maize seeds.

These pots are then placed under glass on sand kept moist by regular sprinkling, at a temperature of 20° C. and a relative humidity of 60%.

Three months after sowing, the seedlings carrying the disease (presence or absence of smut in the maize inflorescences) are counted and the results shown in the table below (expressed as percentage) are obtained. The control seedlings correspond to pots filled with a substrate infected with the disease in which untreated maize seeds have been sown.

| | | Infectious doses (in g/kg) | |
|---|---|---|---|
| | | 0.125 | 0.25 |
| Number of diseased seedlings (in %) | Control seedlings | 67 | 71 |
| | Treated seedlings | 46 | 40 |

EXAMPLE 6

This example illustrates application against root rot (*Fusarium moniliforme*).

Maize seeds (variety Pinnacle) were treated in the proportion of 125 and 250 g of active material per 100 kg of seeds.

These seeds are sown in 7×7 cm pots filled with vermiculite in the proportion of 5 seeds per pot. Infection is carried out by introducing, into the vicinity of the seeds, in the upper part of the substrate, 10 ml of an aqueous suspension containing 400000 spores of *Fusarium moniliforme* per ml.

These pots are then maintained at 80% humidity for 3 weeks at 8° C. and then for 2 weeks at 16° C.

The seedlings carrying the disease (unemerged seedlings and seedlings with slowed and deformed growth) are then counted and the results shown in the table below (expressed as percentage) were obtained. The control seedlings correspond to pots in which untreated maize seeds have been sown, which seeds have been infected with the disease.

| | | Number of diseased seedlings (in %) |
|---|---|---|
| Dose of active material applied (in g/100 kg) | 125 | 72 |
| | 250 | 76 |
| Control seedlings | | 92 |

EXAMPLE 7

This example illustrates application against snow mould (*Microdochium nivale*).

Wheat seeds (variety Ixos), naturally infected with *Microdochium nivale*, were treated in the proportion of 5, 10, 25, 50 and 100 g of active material per 100 kg of seeds.

These seeds are sown in 7×7 cm pots filled with a peat/pozzolana mixture in the proportion of 25 seeds per pot.

These pots are maintained at 5° C. and in darkness for 3 weeks and are then placed at 10° C. under artificial light for 1 week. They are finally placed under glass, on sand kept moist by regular sprinkling, at 20° C. and 60% relative humidity for 1 week.

The seedlings carrying the disease (unemerged seedlings and deformed seedlings) are then counted and the results shown in the table below (expressed as percentage) are obtained. The control seedlings correspond to pots in which wheat seeds, naturally infected with the disease, have been sown, which seeds have not been treated.

| | | Number of diseased seedlings (in %) |
|---|---|---|
| Dose of active material applied (in g/100 kg) | 5 | 89 |
| | 10 | 82 |
| | 25 | 89 |
| | 50 | 85 |
| | 100 | 80 |
| Control seedlings | | 96 |

EXAMPLE 8 This example illustrates application against brown rust of wheat (*Puccinia recondita forma speciae tritici*).

Wheat seeds (variety Theseus) were treated in the proportion of 10, 25, 50 and 100 g of active material per 100 kg of seeds.

These seeds are sown in 7×7 cm pots filled with a peat/pozzolana mixture in the proportion of 40 to 50 seeds per pot.

These pots are maintained at 10° C. under artificial light for 3 weeks, so that they arrive at the growth stage known as the 1–2-leaf stage.

Infection is then carried out by spraying an aqueous suspension containing 100000 spores of *Puccinia recondita* per ml.

The pots are then placed at 20° C. and 100% relative humidity for 24 hours and then under glass, on sand kept moist by regular sprinkling, at 20° C. and 80% relative humidity for 10 days.

The infected foliar area of the 1st leaf is then quantified visually.

The results shown in the table below (expressed as percentage) are obtained. The control seedlings correspond to pots in which untreated wheat seeds have been sown, which seeds have been infected by the disease.

| | | Infection of the 1st leaf (in %) |
|---|---|---|
| Dose of active material applied (in g/100 kg) | 10 | 47 |
| | 25 | 37 |
| | 50 | 17 |
| | 100 | 2 |
| Control seedlings | | 61 |

EXAMPLE 9

This example illustrates application against leaf stripe (*Pyrenophora graminea*).

Barley seeds (variety Agneta), naturally infected with *Pyrenophora graminea*, were treated in the proportion of 100 g of active material per 100 kg of seeds.

These seeds are sown in 7×7 cm pots filled with a peat/pozzolana mixture in the proportion of 25 seeds per pot.

These pots are maintained at 5° C. and in darkness for 3 weeks and are then placed at 10° C. under artificial light for 1 week. They are finally placed under glass, on sand kept moist by regular sprinkling, at 20° C. and 60% relative humidity for 3 weeks.

The seedlings carrying the disease (seedlings carrying off-white streaks along the leaves) are then counted and the following results (expressed as percentage) are obtained. The control seedlings correspond to pots in which barley seeds, naturally infected with the disease, have been sown, which seeds have not been treated. Two successive tests were carried out.

| | Number of diseased seedlings (in %) | |
|---|---|---|
| | Test No. 1 | Test No. 2 |
| Control seedlings | 50 | 44 |
| Treated seedlings | 34 | 29 |

EXAMPLE 10

This example illustrates application against damping off (*Rhizoctonia solani*).

Cotton seeds (variety DP 50) were treated in the proportion of 125, 250 and 500 g of active material per 100 kg of seeds.

These seeds are sown in 7×7 cm pots filled with a peat/pozzolana mixture which has been pre-infected by incorporation of 1 part of an aqueous suspension containing milled *Rhizoctonia solani* mycelium in 1600 parts of substrate. Each pot contains 5 cotton seeds.

These pots are then placed under glass at a temperature of 25° C. and at a relative humidity of 80% for 17 days.

The seedlings which have not emerged (so-called pre-emergence damping off) and the number of seedlings exhibiting a brown necrosis at the base of the collar (so-called post-emergence damping off) are then counted. The results with respect to early damping off (pre-emergence) and with respect to all the damping off attacks (pre-+post-emergence) are shown in the table below (expressed as percentage). The control seedlings correspond to pots filled with a substrate infected with the disease in which untreated cotton seeds have been sown.

| | | Pre-emergence damping off (in %) | Total damping off (in %) |
|---|---|---|---|
| Dose of active material applied (in g/100 kg) | 125 | 45 | 50 |
| | 250 | 45 | 60 |
| | 500 | 10 | 50 |
| Control seedlings | | 70 | 80 |

EXAMPLE 11

This example illustrates application against fungi which degrade wood.

Agar culture medium containing different doses of the active material to be tested is introduced into petri dishes.

Petri dishes with the same culture medium without the active material are prepared in order to act as control.

One day after the preparation of these petri dishes, agar implants supporting a fungal culture are deposited at the center of each petri dish. The fungi tested are: *Serpula lacrymans, Coniophora puteana* (dry and wet rots) and *Gleophyllum trabeum*.

The petri dishes are then placed at 20° C. until the results are recorded. The results are read when the untreated control culture has colonized virtually all the dish. The diameter of the fungal cultures is then measured and the concentration of active material causing 50% inhibition of the growth of the fungus (called the $IC_{50}$) is calculated.

The results obtained are as follows:

| | $IC_{50}$ (in mg/l) |
|---|---|
| *Serpula lacrymans* | 14.5 |
| *Coniophora puteana* | 16.3 |
| *Gloeophyllum trabeum* | 0.3 |

These results demonstrate that the active material tested is effective in controlling fungi of wood.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for protecting plants or wood in need of protection against fungal or bacterial attack, which comprises applying to fungi or bacteria which attack plants or wood, or to a locus thereof attacked by said fungi or bacteria, in a fungicidally or bactericidally effective amount, a compound having the formula:

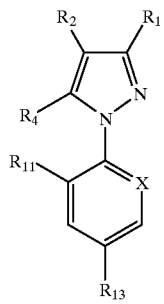

wherein:

$R_1$ is CN or methyl;

$R_2$ is $S(O)_n R_3$;

$R_3$ is $C_1$–$C_6$ alkyl or $C_1$–$C_6$ haloalkyl;

$R_4$ is hydrogen, halogen, $NR_5R_6$, $S(O)_m R_7$, $C(O)R_7$, $C(O)O$—$R_7$, $C_1$–$C_6$ alkyl, $C_1$–$C_6$ haloalkyl, $OR_8$ or —N=C($R_9$)($R_{10}$);

$R_5$ and $R_6$ each independently represent hydrogen, $C_1$–$C_6$ alkyl, $C_1$–$C_6$ haloalkyl, $C(O)(C_1$–$C_6$ alkyl) or $S(O)_r CF_3$; or $R_5$ and $R_6$ together form a divalent alkylene radical which is optionally interrupted by one or two divalent heteroatoms, each of which is oxygen or sulfur, $NR_5R_6$ then having a total of 5 or 6 ring atoms;

$R_7$ is $C_1$–$C_6$ alkyl or $C_1$–$C_6$ haloalkyl;

$R_8$ is $C_1$–$C_6$ alkyl, $C_1$–$C_6$ haloalkyl or hydrogen;

$R_9$ is $C_1$–$C_6$ alkyl or hydrogen;

$R_{10}$ is a phenyl or heteroaryl radical optionally having one or more substituents selected from the group consisting of halogen, OH, —O—($C_1$–$C_6$ alkyl), —S—($C_1$–$C_6$ alkyl), cyano and $C_1$–$C_6$ alkyl;

X is a trivalent nitrogen atom or a C—$R_{12}$ radical, the three other valencies of the carbon atom forming part of the aromatic ring;

$R_{11}$ and $R_{12}$ are each, independently of each other, hydrogen or halogen;

$R_{13}$ is halogen, $C_1$–$C_6$ haloalkyl, $C_1$–$C_6$ haloalkoxy, $S(O)_q CF_3$ or $SF_5$; and m, n, q and r each represent, independently of one another, an integer equal to 0, 1 or 2;

with the proviso that, when $R_1$ is methyl, then $R_3$ is haloalkyl, $R_4$ is $NH_2$, $R_{11}$ is Cl, $R_{13}$ is $CF_3$ and X is N.

2. A method according to claim 1, wherein the compound is applied to fungi or bacteria which attack rice, maize, cereal or cotton crops, or to a rice, maize, cereal or cotton crop locus attacked by said fungi or bacteria.

3. A method according to claim 2, wherein the compound is applied to fungi or bacteria which attack rice crops, or to a rice crop locus attacked by said fungi or bacteria.

4. A method according to claim 3, wherein the fungi or bacteria are fungi or bacteria which cause sheath blight, brown spot, neck blast, leaf blast or leaf scald.

5. A method according to claim 2, wherein the compound is applied to fungi or bacteria which attack maize crops, or to a maize crop locus attacked by said fungi or bacteria.

6. A method according to claim 5, wherein the fungi or bacteria are fungi, or bacteria which cause head smut or root rot.

7. A method according to claim 2, wherein the compound is applied to fungi or bacteria which attack wheat crops, or to a wheat crop locus attacked by said fungi or bacteria.

8. A method according to claim 7, wherein the fungi or bacteria are fungi or bacteria which cause root rot or root rust.

9. A method according to claim 2, wherein the compound is applied to fungi or bacteria which attack barley crops, or to a barley crop locus attacked by said fungi or bacteria.

10. A method according to claim 9, wherein the fungi or bacteria are fungi or bacteria which cause leaf stripe.

11. A method according to claim 2, wherein the compound is applied to fungi or bacteria which attack cotton plants, or to a cotton plant locus attacked by said fungi or bacteria.

12. A method according to claim 11, wherein the fungi or bacteria are fungi or bacteria which cause damping off.

13. A method according to claim 1, wherein the compound is applied to bacteria which attack plants or wood, or to a locus attacked by said bacteria.

14. A method according to claim 13, wherein the bacteria are Pseudomonas or Erwinia species.

15. A method according to claim 1, wherein $R_1$ is CN.

16. A method according to claim 1, wherein $R_3$ is haloalkyl.

17. A method according to claim 1, wherein $R_4$ is $NH_2$.

18. A method according to claim 1, wherein $R_{11}$ is halogen.

19. A method according to claim 1, wherein $R_{12}$ is halogen.

20. A method according to claim 1, wherein $R_{13}$ is haloalkyl.

21. A method according to claim 1, wherein $R_1$ is CN, $R_3$ is haloalkyl, $R_4$ is $NH_2$, $R_{11}$ is halogen, $R_{12}$ is halogen and $R_{13}$ is haloalkyl.

22. A method according to claim 1, wherein the compound of formula (I) is 5-amino-3-cyano-1-(2,6-dichloro-4-trifluoromethyl)phenyl-4-trifluoromethylsulfinylpyrazole.

23. A method according to claim 1, wherein plants are protected by applying the compound of formula (I) to a locus attacked by said fungi or bacteria which comprises plant foliage, plant seed or the soil in which plants grow.

24. A method according to claim 23, wherein the compound of formula (I) is applied at a rate of from about 5 g/ha to about 500 g/ha.

25. A method according to claim 24, wherein the compound of formula (I) is applied at a rate of from about 10 g/ha to about 200 g/ha.

26. A method according to claim 25, wherein the compound of formula (I) is applied at a rate of from about 20 g/ha to about 80 g/ha.

27. A method according to claim 1, wherein wood is protected by applying to wood attacked by said fungi or bacteria from about 10 g/m$^3$ to about 800 g/m$^3$ of the compound of formula (I).

28. A method according to claim 27, wherein from about 50 g/m$^3$ to about 500 g/m$^3$ of the compound of formula (I) are applied.

29. A method according to claim 23, wherein the compound of formula (I) is applied to plant seeds in a proportion of from about 1 g to about 1000 g per 100 kg of seeds.

30. A method according to claim 29, wherein from about 2 g to about 800 g of compound of formula (I) are applied per 100 kg of seeds.

31. A method according to claim 30, wherein from about 5 g to about 500 g of compound of formula (I) are applied per 100 kg of seeds.

32. A method according to claim 23, wherein the compound of formula (I) is applied to rice seeds in a proportion of from about 2 g to about 200 g per 100 kg of seeds.

33. A method according to claim 32, wherein from about 5 g to about 80 g of compound of formula (I) are applied per 100 kg of seeds.

34. A method according to claim 23, wherein the compound of formula (I) is applied to cereal seeds in a proportion of from about 5 g to about 250 g per 100 kg of seeds.

35. A method according to claim 34, wherein from about 10 g to about 100 g of compound of formula (I) are applied per 100 kg of seeds.

36. A method according to claim 23, wherein the compound of formula (I) is applied to maize seeds in a proportion of from about 50 g to about 1000 g per 100 kg of seeds.

37. A method according to claim 36, wherein from about 100 g to about 500 g of compound of formula (I) are applied per 100 kg of seeds.

38. A method according to claim 23, wherein the compound of formula (I) is applied to cotton seeds in a proportion of from about 50 g to about 500 g per 100 kg of seeds.

39. A method according to claim 38, wherein from about 100 g to about 250 g of compound of formula (I) are applied per 100 kg of seeds.

* * * * *